United States Patent [19]
Schutt

[11] Patent Number: 5,540,225
[45] Date of Patent: Jul. 30, 1996

[54] METHOD AND APPARATUS FOR PARTIAL LIQUID VENTILATION OR FLUOROCARBONS

[75] Inventor: Ernest G. Schutt, San Diego, Calif.

[73] Assignee: Alliance Pharmaceutical Corp., San Diego, Calif.

[21] Appl. No.: 180,700

[22] Filed: Jan. 13, 1994

Related U.S. Application Data

[63] Continuation of Ser. No. 791,996, Nov. 14, 1991, abandoned.

[51] Int. Cl.$^6$ .................................................. A61M 16/00
[52] U.S. Cl. ..................................... 128/207.15; 128/913
[58] Field of Search .......................... 128/207.14, 207.15, 128/913

[56] References Cited

U.S. PATENT DOCUMENTS

| | | | |
|---|---|---|---|
| 3,975,512 | 8/1976 | Long | 424/5 |
| 4,036,210 | 7/1977 | Campbell et al. | 128/207.16 |
| 4,821,715 | 4/1989 | Downing | 128/207.18 |
| 4,825,859 | 5/1989 | Lambert | 128/202.16 |
| 5,024,995 | 6/1991 | Robertson et al. | 514/21 |
| 5,029,580 | 7/1991 | Radford et al. | 128/207.14 |

FOREIGN PATENT DOCUMENTS

| | | |
|---|---|---|
| 858824 | 8/1981 | U.S.S.R. . |
| 1143420 | 3/1985 | U.S.S.R. . |
| 9103267 | 3/1991 | WIPO . |

OTHER PUBLICATIONS

"Compliance and Diffusion During Respiration With Fluorocarbon Liquid", by Gollan et al., Federation Proceedings, vol. 29, #5, Sep.–Oct. 1970.

Reiss, J. G. *Artifical Organs* 8: 34–56, 1984.
Curtis et al. *J. Appl. Physiol.* 68(6):2322–8 1990.
Curtis et al. *Crit. Care Med.* 19(2): 225–230 1991.
Merritt et al. *Drugs* 38(4): 591–611 1989.
Nakayama et al. *Crit. Care Med.* 19: 926–933 1991.
Ravenscraft et al. *Crit. Care Med.* 19: 916–925 1991.
Richman et al. Lung Lavage with Oxygenated Fluorocarbon Improves Gas Exchange and Lung Compliance in Cats with Acute Lung Injury 1990.
Rufer et al. *Chest* 66(suppl): 29S–30S 1974.
Shaffer et al. *J. Appl. Physiol.* 36: 208–213 1974.
Shaffer et al. *Pediat. Res.* 10: 227–231 1976.
Shaffer et al. *Chest Res.* 17: 303–306 1983.
Shaffer et al. *Undersea Biomed. Res.* 14: 169–170 1987.
Waldrop, M. M. *Science* 245: 1043–1045 1989.
Widjaja et al. *Res. Exp. Med.* 188: 425–432 1988.
Yokoyama et al. *Artificial Organs* 8(1): 34–40 1984.
Fuhrman, M. D., F.C.C.M. et al., Perfluorocarbon–associated gas exchange, *Critical Care Medicine* 19: 712–722 (1991).
Abstract of Fuhrman, M.D., F.C.C.M. et al., Perfluorocarbon–associated gas exchange, 1 page (Apr. 5, 1991) (approx.).

*Primary Examiner*—Aaron J. Lewis
*Attorney, Agent, or Firm*—Knobbe, Martens, Olson & Bear

[57] ABSTRACT

A method and apparatus for performing partial liquid ventilation, in connection with which a liquid such as an oxygen carrying fluorocarbon liquid is introduced into the lung and removed from the lung of a patient while the patient is simultaneously breathing an oxygen-carrying breathing gas.

49 Claims, 3 Drawing Sheets

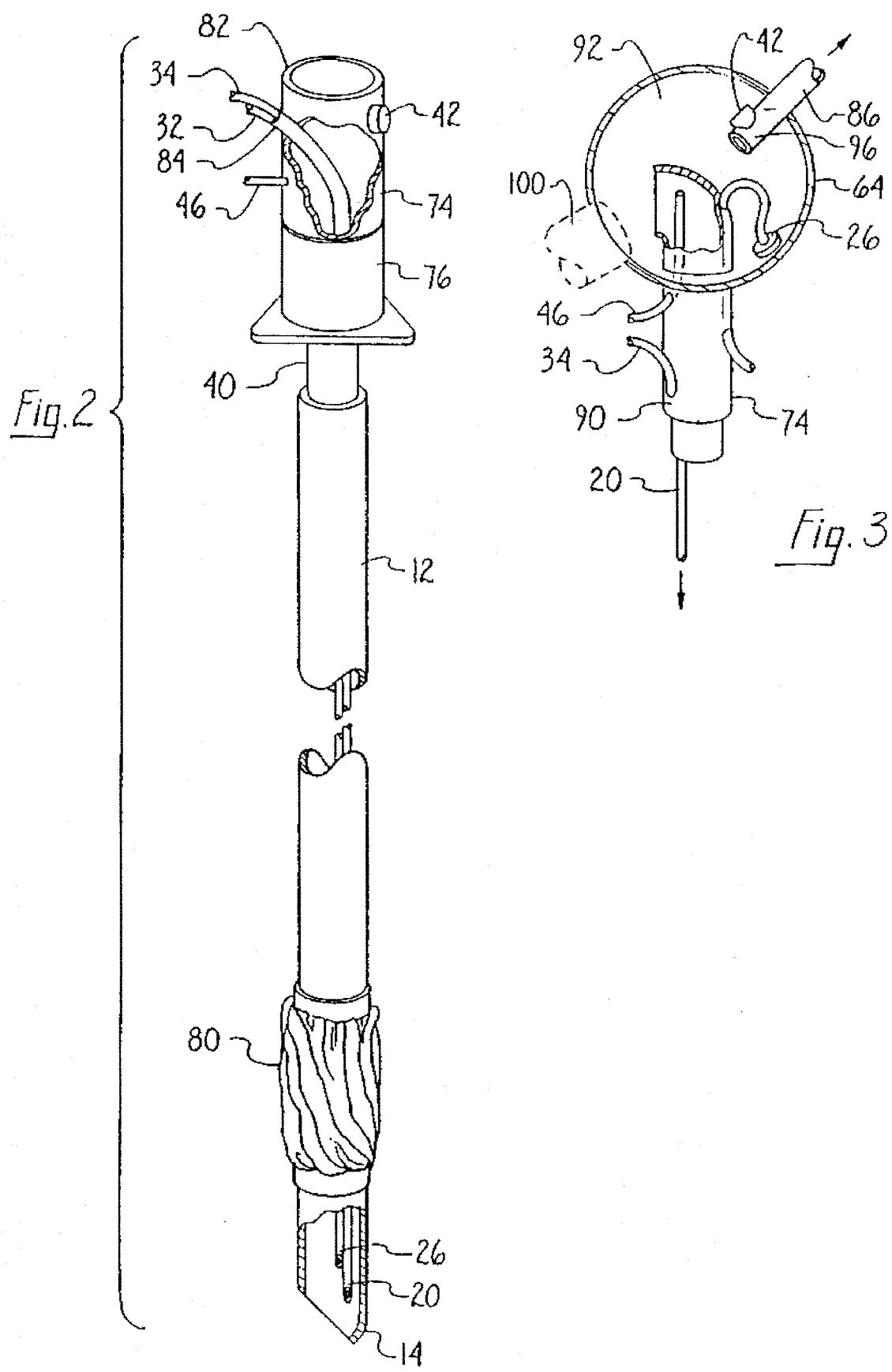

METHOD AND APPARATUS FOR PARTIAL LIQUID VENTILATION OR FLUOROCARBONS

This application is a continuation of application Ser. No. 07/791,996, filed Nov. 14, 1991 now abandoned.

FIELD OF THE INVENTION

The present invention relates to apparatus and method for performing partial liquid ventilation techniques, and specifically relates to the use of such apparatus with biocompatible liquid fluorocarbons in treatment of various pulmonary conditions.

BACKGROUND OF THE INVENTION our related U.S. patent application Ser. No. 07/695,547 discloses methods for performing partial liquid ventilation with fluorocarbon liquids. These methods do not require complicated liquid-handling ventilation equipment with associated oxygenators and other paraphernalia; instead, traditional ventilation equipment can be used. Perfluorocarbon liquid is instilled into the lung and remains there in a quantity approximately equal to or less than the functional residual capacity of the lungs (the lung volume plus endotracheal tube volume upon exhalation). Gas then moves into and out of the lung to oxygenate the perfluorocarbon liquid in the lung. The perfluorocarbon liquid permits respiration by the patient even though the lungs are damaged or surfactant deficient.

Lung surfactant functions to reduce surface tension within the alveoli. It mediates transfer of oxygen and carbon dioxide, promotes alveolar expansion and covers the lung surfaces. Reduced surface tension permits the alveoli to be held open under less pressure. In addition, lung surfactant maintains alveolar expansion by varying surface tension with alveolar size (*The Pathologic Basis of Disease*, Robbins and Cotran eds. W. B. Saunders Co. New York, 1979). There are a number of medical therapies or regimes that would benefit from the use of surfactant supplements. For example, surfactant supplementation is beneficial for individuals with lung surfactant deficiencies. In addition, there are a variety of medical procedures requiring that fluids be added to the lung, for example, as a wash to remove endogenous or exogenous matter. The use of a biocompatible liquid for these applications would be advantageous. Routinely, balanced salt solutions or balanced salt solutions in combination with a given therapeutic agent are provided as an aspirate or as a lavage for patients with asthma, cystic fibrosis or bronchiectasis. While balanced saline is biocompatible, lavage procedures can remove endogenous lung surfactant. Further, lavage with such aqueous liquids may not permit adequate delivery of oxygen to the body. Therefore, it is contemplated that the use of substances having at least some of the functional properties of lung surfactant could decrease lung trauma and provide an improved wash fluid.

At present, surfactant supplements are used therapeutically in infants when the amount of lung surfactant present is not sufficient to permit proper respiratory function. Surfactant supplementation is most commonly used in Respiratory Distress Syndrome (RDS), a specific form of which is known as hyaline membrane disease, when surfactant deficiencies compromise pulmonary function. While RDS is primarily a disease of newborn infants, an adult form of the disease, Adult Respiratory Distress Syndrome (ARDS), has many of the same characteristics as RDS, thus lending itself to similar therapies.

Adult respiratory distress syndrome can occur as a complication of shock-inducing trauma, infection, burn or direct lung damage. The pathology is observed histologically as diffuse damage to the alveolar wall, with capillary damage. Hyaline membrane formation, whether in ARDS or RDS, creates a barrier to gas exchange. Decreased oxygen produces a loss of lung epithelium yielding decreased surfactant production and foci of collapsed alveoli. This initiates a vicious cycle of hypoxia and lung damage.

RDS accounts for up to 5,000 infant deaths per year and affects up to 40,000 infants each year in the United States alone. While RDS can have a number of origins, the primary etiology is attributed to insufficient amounts of pulmonary surfactant. Those at greatest risk are infants born before the 36th week of gestation having premature lung development. Neonates born at less than 28 weeks of gestation have a 60-80% chance of developing RDS. The maturity of the fetal lung is assessed by the lecithin/sphingomyelin (L/S) ratio in the amniotic fluid. Clinical experience indicates that when the ratio approximates 2:1, the threat of RDS is small. In those neonates born from mothers with low L/S ratios, RDS becomes a life-threatening condition.

At birth, high inspiratory pressures are required to expand the lungs. With normal amounts of lung surfactant, the lungs retain up to 40% of the residual air volume after the first breath. With subsequent breaths, lower inspiratory pressures adequately aerate the lungs since the lungs now remain partially inflated. With low levels of surfactant, whether in infant or adult, the lungs are virtually devoid of air after each breath. The lungs collapse with each breath and the neonate must continue to work as hard for each successive breath as it did for its first. Thus, exogenous therapy is required to facilitate breathing and minimize lung damage.

Type II granular pneumocytes synthesize surfactant using one of two pathways dependent on the gestational age of the fetus. The pathway used until about the 35th week of pregnancy produces a surfactant that is more susceptible to hypoxia and acidosis than the mature pathway. A premature infant lacks sufficient mature surfactant necessary to breathe independently. Since the lungs mature rapidly at birth, therapy is often only required for three or four days. After this critical period the lung has matured sufficiently to give the neonate an excellent chance of recovery.

In adults, lung trauma can compromise surfactant production and interfere with oxygen exchange. Hemorrhage, infection, immune hypersensitivity reactions or the inhalation of irritants can injure the lung epithelium and endothelium. The loss of surfactant leads to foci of atelectasis. Tumors, mucous plugs or aneurysms can all induce atelectasis, and these patients could therefore all benefit from surfactant therapy.

In advanced cases of respiratory distress, whether in neonates or adults, the lungs are solid and airless. The alveoli are small and crumpled, but the proximal alveolar ducts and bronchi are overdistended. Hyaline membranes line the alveolar ducts and scattered proximal alveoli. The membrane contains protein-rich, fibrin-rich edematous fluid admixed with cellular debris.

The critical threat to life in respiratory distress is inadequate pulmonary exchange of oxygen and carbon dioxide resulting in metabolic acidosis. In infants this, together with the increased effort required to bring air into the lungs, produces a lethal combination resulting in overall mortality rates of 20–30%.

Optimally, surfactant supplements should be biologically compatible with the human lung. They should decrease the surface tension sufficiently within the alveoli, cover the lung surface easily and promote oxygen and carbon dioxide exchange.

Fluorocarbons are fluorine substituted hydrocarbons that have been used in medical applications as imaging agents and as blood substitutes. U.S. Pat. No. 3,975,512 to Long uses fluorocarbons, including brominated perfluorocarbons, as a contrast enhancement medium in radiological imaging. Brominated fluorocarbons and other fluorocarbons are known to be safe, biocompatible substances when appropriately used in medical applications.

It is additionally known that oxygen, and gases in general, are highly soluble in some fluorocarbons. This characteristic has permitted investigators to develop emulsified fluorocarbons as blood substitutes. For a general discussion of the objectives of fluorocarbons as blood substitutes and a review of the efforts and problems in achieving these objectives see "Reassessment of Criteria for the Selection of Perfluorochemicals for Second-Generation Blood Substitutes: Analysis of Structure/Property Relationship" by Jean G. Riess, *Artificial Organs* 8:34–56, 1984.

Oxygenatable fluorocarbons act as a solvent for oxygen. They dissolve oxygen at higher tensions and release this oxygen as the partial pressure decreases. Carbon dioxide is handled in a similar manner. Oxygenation of the fluorocarbon, when used intravascularly, occurs naturally through the lungs. For other applications, such as percutaneous transluminal coronary angioplasty, stroke therapy and organ preservation, the fluorocarbon can be oxygenated prior to use.

Liquid breathing has been demonstrated on several occasions. An animal may be submerged in an oxygenated fluorocarbon liquid and the lungs may be filled with fluorocarbon. Although the work of breathing is increased in these total submersion experiments, the animal can derive adequate oxygen for survival from breathing the fluorocarbon liquid.

Full liquid breathing as a therapy presents significant problems. Liquid breathing in a hospital setting requires dedicated ventilation equipment capable of handling liquids. Moreover, oxygenation of the fluorocarbon being breathed must be accomplished separately. The capital costs associated with liquid breathing are considerable.

Safe and convenient clinical application of the partial liquid ventilation techniques disclosed in related U.S. application Ser. No. 07/695,547 could benefit from a simple apparatus for practicing that method. The present invention includes such an apparatus, together with a new method of using the apparatus in partial liquid ventilation.

These and other objects of the invention are discussed in the detailed description of the invention that follows.

SUMMARY OF THE INVENTION

The present invention includes an apparatus for introduction and removal of liquids from the lung of a patient, comprising means for introducing a liquid into the lung while the patient is simultaneously breathing a gas, and means for removing the liquid from the lung while the patient is simultaneously breathing a gas. In one embodiment, the removing means comprises means for removing excess liquid to maintain a relatively constant volume of liquid in the lung while simultaneously breathing gas. According to a particular embodiment, the introducing means is adapted to continuously introduce the liquid. In another embodiment, the introducing means is adapted to introduce the liquid simultaneously with the inhalation of the gas, and may pulse the introduction of the liquid. Further, the apparatus may be adapted to remove the liquid during a portion of the breathing cycle in which the lung is substantially deflated. One embodiment of the removing means includes an inlet adapted to be positioned in the patient's trachea or in close proximity thereto to remove liquid from the trachea that comes in contact with the inlet. The apparatus may further include an endotracheal tube in which the inlet is located, the tube adapted to be located at a fixed position in the trachea, to remove liquid while such liquid is in contact with the inlet so that during the breathing cycle at the end of expiration, the liquid level in the pulmonary system of the patient is approximately at the level of the inlet.

A further variation of the removing means includes a gas/liquid separator adapted to be interposed in the pathway of fluid flowing into and out of the lungs. The gas/liquid separator is adapted to separate fluorocarbon liquid exiting the lungs from gas exhaled by the patient, so that at the end of exhalation the liquid level in the patient's breathing passageway extends substantially up to but not beyond the gas/liquid separator. The apparatus may further include an endotracheal tube connected to the gas/liquid separator. The introducing means can be adapted to continuously introduce liquid, and the removing means may be adapted to remove liquid at an average rate greater than or equal to the rate of introduction by the introducing means.

In another embodiment, the apparatus includes means for pulsing the introduction of liquid into the lungs in synchrony with a portion of the breathing cycle. The apparatus further can include means for pulsing the removal of liquid from the lungs in synchrony with a portion of the breathing cycle. Also contemplated is a temperature control device to control the temperature of the liquid introduced into the lungs. Further, a reservoir can be provided into which the removing means directs the removed liquid. The introducing means can be adapted to remove liquid from the reservoir for introduction into the lungs. It is desirable to include means for separating contaminating material from the liquid in the reservoir prior to reintroduction into the lungs.

In a further embodiment, the liquid is a fluorocarbon liquid and the separating means is adapted to separate floating contaminants from a fluorocarbon liquid. Further, the reservoir can have a fluorocarbon/aqueous aspirant interface and the introducing means removes fluorocarbon liquid from the reservoir from a point below the level of the fluorocarbon/aqueous aspirant interface.

Further included in the invention is an embodiment wherein the introducing means and removing means are attached to the endotracheal tube. A gas ventilation device can be connected to the endotracheal tube to introduce breathing gas to the lungs and to remove gas from the lungs. In the embodiment including a fluorocarbon reservoir for receiving fluid removed from the patient by the removing means, there can be a gas vent connecting the reservoir to the endotracheal tube to permit outside equalization of pressure between the endotracheal tube and the fluorocarbon reservoir.

The apparatus can also include a gas flow sensor associated with the endotracheal tube that pauses the introduction of liquid into the lung during exhalation. Similarly, the apparatus may include a gas flow sensor associated with the endotracheal tube that pauses the removal of liquid from the lung during inhalation.

The present invention may also constitute an endotracheal tube for use in partial liquid ventilation, comprising a tube having a central bore and a proximal end and a distal end, the tube adapted to be inserted into the trachea of a patient and to carry breathing gas into and out of the pulmonary system of the patient, a seal on the outside of the tube for sealing against the patient's trachea and preventing fluid from moving into and out of the patient's lungs outside of the tube, a liquid instillation conduit associated with the tube for introducing fluid into the lungs of a patient while the patient is breathing a gas through the tube, and a liquid removal conduit associated with the tube for removing fluid from the lungs of a patient while the patient is breathing a gas through the tube. In one embodiment, the endotracheal tube may further comprise a gas/liquid separator connected to the tube in such a way that it is interposed in the pathway of breathing gas entering and leaving the tube, and the liquid removal conduit may be adapted to remove liquid from the gas/liquid separator. Preferably, the liquid instillation conduit is adapted to introduce liquid into the endotracheal tube, and the liquid removal conduit is adapted to remove liquid from the endotracheal tube.

The invention also includes a method for introduction and removal of liquids from the lung of a patient, comprising introducing a liquid into the lung while the patient is simultaneously breathing a gas, and removing the liquid from the lung while the patient is simultaneously breathing a gas. The method may advantageously further comprise the step of providing a liquid removing means having an inlet positioned in the trachea of the patient or in close proximity thereto, wherein the removing step comprises removing liquid from the breathing passageway of the patient that rises to the level of the inlet during the portion of the breathing cycle when the lungs are substantially deflated.

In one version of the method, the patient has an endotracheal tube in place and the inlet of the liquid removing means is positioned between the distal end of the trachea of the patient and about the proximal end of the endotracheal tube. In another embodiment, the liquid removing means includes a pump adapted to remove liquid from the patient at an average rate equal to or greater than the average rate of introduction of liquid into the lungs. Preferably, the liquid is an oxygen-carrying fluorocarbon.

The method of the invention may further include the step of collecting the liquid removed from the patient. The method can include the steps of separating contaminants from the collected liquid, and reintroducing that liquid into the lungs of the patient. Preferably, again, the liquid is a fluorocarbon and the separating step is accomplished by floatation of the contaminants on the fluorocarbon. Alternatively or in conjunction with this embodiment, the separating step includes filtering to separate debris or aqueous materials from the liquid.

Advantageously, the method may further comprise the step of condensing evaporated liquid from the breathing gas exhaled by the patient. In one preferred embodiment, the volume of liquid in the pulmonary system of the patient is maintained at about the functional residual capacity of the patient's pulmonary system. In another embodiment, the volume of liquid in the pulmonary system of the patient is maintained at about the functional residual capacity of the patient's pulmonary system plus the internal volume of the trachea and endotracheal tube. The method may additionally comprising the step of introducing a pharmacologic agent into the lung while performing the method.

BRIEF DESCRIPTION OF THE DRAWINGS

FIG. 2 is a perspective view of an endotracheal tube with a partial liquid ventilation connector mounted on the proximal end of an endotracheal tube.

FIG. 3 is a perspective view of a partial liquid ventilation connector for attachment to an endotracheal tube, including a gas/liquid separator in said adapter.

DETAILED DESCRIPTION OF THE INVENTION

Figure 1:
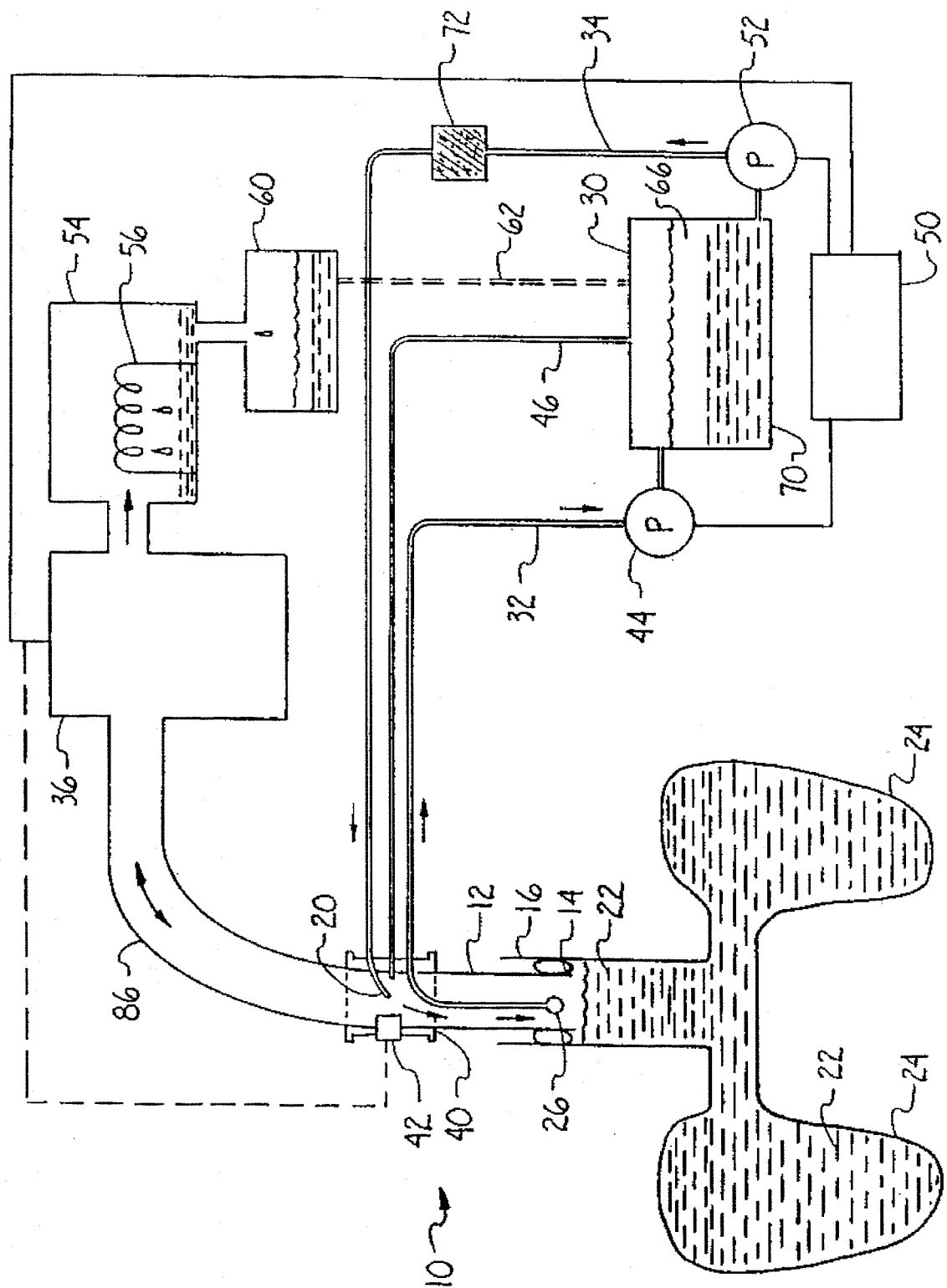
FIG. 1 is a schematic representation of an apparatus for performing partial liquid ventilation.

Partial liquid ventilation has a number of benefits over the total liquid breathing methods contemplated primarily for use in neonates. The lungs are bathed in a biocompatible fluid. Lung trauma is minimized and this permits lung maturation and repair. Partial liquid ventilation is more amenable to use than total liquid breathing since air or gas can still be inhaled and exhaled. Partial liquid ventilation can be used in conjunction with spontaneous, passive or mechanical ventilation and, because it is more natural, precludes the necessity of deep sedation and/or paralysis of respiratory muscles. In addition, pharmacologic substances can be added to the fluorocarbon to further promote resolution of lung injury.

The amount of fluorocarbon introduced into the patient's lung is, at a minimum, necessarily sufficient to cover the surfaces of the lung. The actual volumes will depend on the treatment protocol, the weight and size of a patient, as well as the lung capacity. It is contemplated that the useful range of fluorocarbon should be at least 0.1 ml of fluorocarbon liquid per kilogram patient body weight and not more than about 50 ml/kg.

It is further preferred that the maximum amount of fluorocarbon used for partial liquid ventilation will approximate the volume of air remaining in a healthy lung of similar size following exhalation, or alternatively, that volume plus the volume of the endotracheal tube. The amount of air remaining in the lung at the end of exhalation can be measured in a number of ways that are known by those with skill in the art. Physiology-related equations relate the size, age, or weight of an individual to his exhaled lung volume.

Thus, during partial liquid ventilation in accordance with the present invention, the lungs retain sufficient air capacity (above and beyond the volume of fluorocarbon in the lung) to permit inhalation such that normal breathing can proceed. The amount of air entering the lungs on inhalation is sufficient to oxygenate the fluorocarbon liquid. Further, the fluorocarbon liquid may be oxygenated prior to use to provide oxygen to the alveolar surfaces of the lung instantaneously upon initial contact with the fluorocarbon. If ventilation therapy is required, unlike total liquid breathing, standard ventilation equipment can be used. Partial liquid ventilation can be used to reverse ventilary failure, as a prophylactic to prevent respiratory failure or as a therapeutic. As a therapeutic, fluorocarbon liquid can be administered alone to minimize further lung trauma, or in combination with a given therapeutic agent. Fluorocarbon liquid can be provided together with a particulate therapeutic agent such as lung surfactant. These powder surfactants may be synthetic mixtures of phospholipids. For example, a mixture of diphosphatidylcholine and phosphoglycerol in a ratio of 7:3 could be mixed with a volume of fluorocarbon. Additionally, the surfactant powder may be in the form of dried extracts prepared from human or animal lung lavage. There are three major proteins (SP-A, SP-B and SP-C) associated with endogenous lung surfactant. Therefore, it is additionally contemplated that these proteins may be added as full length or as truncated fragments to the fluorocarbon mixture.

Compounds useful in this invention, such as those listed below (referred to herein as "fluorocarbons") are generally able to promote gas exchange, and most of these fluorocarbons readily dissolve oxygen and carbon dioxide. There are a number of fluorocarbons that are contemplated for medical use. These fluorocarbons include bis(F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E"); cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di-or F-trimethylbicyclo[3,3,1]nonane ("nonane"); perfluorinated amines, such as F-tripropylamine("FTPA") and F-tri-butylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101").

Other fluorocarbons include brominated perfluorocarbons, such as 1-bromo-heptadecafluoro-octane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms. In addition, the fluorocarbon may be neat or may be combined with other materials, such as surfactants (including fluorinated surfactants) and dispersed materials.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example, compounds having the general formula $C_nF_{2n+1}C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated and are considered to fall within the meaning of "fluorocarbon" as used herein. Additional "fluorocarbons" not listed here, but having those properties described in this disclosure that would lend themselves to pulmonary therapies are additionally contemplated.

Some fluorocarbons have relatively high vapor pressures which render them less suitable for use as a surfactant replacement and for partial liquid ventilation. These include 1-bromotridecafluorohexane ($C_6F_{13}Br$) and F-2-butyltetrahydrofuran ("FC-75" or "RM101"). Lower vapor pressures are additionally important from an economic standpoint since significant percentages of fluorocarbon having high vapor pressure would be lost due to vaporization during the therapies described herein. In a preferred embodiment, fluorocarbons having lower surface tension values are chosen as surfactant supplements.

The fluorocarbon of choice should have functional characteristics that would permit its use temporarily as a lung surfactant, for oxygen delivery, in removal of material from the interior of the lung, or for inflation of collapsed portions of the lung. Fluorocarbons are biocompatible and most are amenable to sterilization techniques. For example, they can be heat-sterilized (such as by autoclaving) or sterilized by radiation. In addition, sterilization by ultrafiltration is also contemplated.

One group of preferred fluorocarbons have the ability to reduce the surface tension in the lung. As noted above, surfactants function to decrease the tension between the surface molecules of the alveolar fluid. The lung surfactant is solubilized in a water-continuous fluid lining the alveolus. Typically, the surface tension in the absence of lung surfactant is ca. 70 dynes/cm decreasing to 5–30 dynes/cm in the presence of lung surfactant. Fluorocarbons have low surface tension values (typically in the range of 20 dynes/cm) and have the added benefit of dissolving extremely large quantities of gases such as oxygen and carbon dioxide. Perfluorocarbons are particularly suited for this use, and brominated fluorocarbons are particularly preferred.

Although reduction in surface tension is an important parameter in judging fluorocarbons and perfluorocarbons as potential lung surfactant supplements or for use in partial liquid ventilation, a novel and non-obvious characteristic of some fluorocarbons is their apparent ability to spread over the entire respiratory membrane. The ability of some fluorocarbons to spread evenly and effectively over lung surfaces may be of even greater importance than the ability of fluorocarbons to reduce surface tension.

The total surface area of the respiratory membrane is extremely large (ca. 160 square meters for an adult). Thus, an effective fluorocarbon for partial liquid ventilation should be able to cover the lung surfaces with relatively little volume.

The ability of a given substance to cover a measured surface area can be described by its spreading coefficient. The spreading coefficients for fluorocarbons can be expressed by the following equation:

$$S(o \text{ on } w) = \gamma_{w/a} - (\gamma_{w/o} + \gamma_{o/a})$$

Where S (o on w) represents the spreading coefficient; $\gamma$=interfacial tension; w/a=water/air; w/o =water/oil; and o/a=oil/air.

If the fluorocarbon exhibits a positive spreading coefficient, then it will spread over the entire surface of the respiratory membrane spontaneously. Fluorocarbons having spreading coefficients of at least one are particularly preferred. If the spreading coefficient is negative, the compound will tend to remain as a lens on the membrane surface. Adequate coverage of the lung surface is important for restoring oxygen and carbon dioxide transfer and for lubricating the lung surfaces to minimize further pulmonary trauma.

The spreading coefficients for a number of perfluorocarbons are reported in Table 1. Each perfluorocarbon tested is provided together with its molecular weight and the specific variables that are used to calculate the spreading coefficient S (o on w). The perfluorocarbons reported are PFOB, perfluorotributylamine (FC-43), perfluorodecalin (APF-140), dimethyl perfluorodecalin (APF-175), trimethyl decalin (APF-200), perfluoroperhydrophenanthrene (APF-215), pentamethyl decalin (APF-240), and octamethyl decalin (APF-260).

These perfluorocarbons are representative of groups of perfluorocarbons having the same molecular weight that would produce similar spreading coefficients under similar experimental conditions. For example, it is expected that ethyl perfluorodecalin will have a spreading coefficient similar to that of dimethylperfluorodecalin. Propyl or other 3 carbon-substituted decalin would have a spreading coefficient similar to that reported for trimethyl decalin, pentamethyldecalin is representative of other decalins substituted with 5 substituent carbons, and octamethyldecalin is also representative of other combination substituted decalins of identical molecular weight.

TABLE I

Spreading coefficients of perfluorocarbons on saline (T = 25° C.)

| Perfluorocarbon | MW (g/mol) | γ$_{o/a}$ (mN/m) | γ$_{o/w}$ (mN/m) | S(o on w) |
|---|---|---|---|---|
| PFOB (perfluorooctyl-bromide) | 499 | 18.0 | 51.3 | +2.7 |
| FC-47 (perfluorotributyl-amine) | 671 | 17.9 | 55.1 | −1.0 |
| APF-140 (perfluorodecalin) | 468 | 18.2 | 55.3 | −1.5 |
| APF-175 (dimethyl decalin) | 570 | 20.7 | 55.9 | −4.6 |
| APF-200 (trimethyl decalin) | 620 | 21.4 | 55.9 | −5.3 |
| APF-215 (perfluoroperhydro-phenanthrene) | 630 | 21.6 | 56.0 | −5.6 |
| APF-240 (pentamethyl decalin) | 770 | 22.6 | 56.3 | −6.9 |
| APF-260 (octamethyl decalin) | 870 | 22.4 | 56.1 | −6.5 |

It can be seen from this limited sampling of fluorocarbons that perfluorooctylbromide (PFOB) provides a positive spreading coefficient. In addition, PFOB has a low vapor pressure (10.5 torr @ 37° C.), further illustrating that PFOB is a particularly preferred choice for use as a lung surfactant replacement. Because of the reduced vapor pressure, PFOB will have a decreased tendency to vaporize during use. Perfluorodecalin (APF-140) and perfluorotripropylamine (FC-47) have also been tested in potential blood substitute formulations. These compounds exhibit negative spreading coefficients on saline. However, other perfluorocarbons, similar to APF-140 and FC-47, but having decreasing molecular weights, exhibited decreasing surface tensions and increasing spreading coefficients. This suggests that lower molecular weight perfluorocarbons might also have useful spreading coefficients. However, decreasing molecular weight will increase vapor pressure and make the compounds less suitable for this use.

It is contemplated that there are a variety of uses for fluorocarbons in partial liquid ventilation applications. Lung lavage can be used as both a diagnostic and therapeutic procedure. Diagnostic washings are often obtained by bronchoscopy. Diagnostic lavage requires the introduction of a small amount of fluid into the lungs in order to sample lung cells, exudate, or to obtain a sample for microbiological analysis.

Therefore, in accordance with one aspect of this invention, it is contemplated that PFOB or another fluorocarbon meeting the positive criteria disclosed herein could be used for such a procedure.

Large volume lung lavage is sometimes used as an emergency procedure to remove irritants, poisons or mucous plugs from the lungs. The procedure is also used in neonates to remove aspirated meconium. A pulmonary catheter is inserted into the bronchialairway and a solution is flushed into the lung. The use of saline in the lung for large volume lavage creates several problems. The procedure must be performed quickly because oxygen transfer at the membrane/air interface cannot occur efficiently in the presence of saline, and large volumes of saline flushed into the lungs effectively dilute and remove any functional lung surfactant present.

It is also contemplated that fluorocarbons could be used to inflate collapsed portions of lungs or collapsed lungs in general. The use of fluorocarbon to inflate portions of the lung is less damaging than the current methods employing increased air pressure. As noted previously, increased air pressures in lungs, particularly lungs that are compromised by disease or trauma, can produce barotrauma and induce additional lung damage. It is anticipated that fluorocarbons with positive spreading coefficients will reduce the morbidity of RDS patients using current lung surfactant replacements which do not spread by reducing barotrauma.

If the lungs have been compromised by an irritant, then surfactant replacement may be necessary. Oxygenatable fluorocarbons with positive spreading coefficients and low vapor pressures could provide an improved lavage fluid.

The fluorocarbon could also be provided as a liquid or aerosol in combination with an expectorant. The biocompatible fluorocarbon is easily taken into the lung and the expectorant additive facilitates the removal of the secretions of the bronchopulmonary mucous membrane. Examples of contemplated expectorants include but are not limited to ammonium carbonate, bromhexine hydrochloride and terpin hydrate.

In accordance with another aspect of this invention, it is further contemplated that PFOB or another suitable fluorocarbon could be used as a surfactant supplement. PFOB is able to spread easily over the surfaces of the lung and can facilitate oxygen transport. Any condition characterized by a lung surfactant deficiency would be amenable to this therapy. In addition to RDS in neonates, ARDS in adults caused by severe hypovolemic shock, lung contusion, diver's lung, post-traumatic respiratory distress, post-surgical atelectasis, septic shock, multiple organ failure, Mendelssohn's disease, obstructive lung disease, pneumonia, pulmonary edema or any other condition resulting in lung surfactant deficiency or respiratory distress are all candidates for fluorocarbon supplementation.

The amount of surfactant supplement given should be sufficient to cover the lung surface and should be at least 0.1% of the infant or adult's total lung capacity. In RDS, it is particularly important to stabilize the infant while minimizing and preventing additional lung damage for roughly four or five days. Those infants with RDS that survive this critical time frame have an 80% survival rate. The fluorocarbon is provided by direct instillation through an endotracheal tube. If the fluorocarbon is provided together with a surfactant powder, the powder can either be mixed into the fluorocarbon or provided to the infant or adult as an aerosol prior to fluorocarbon administration. The addition of lung surfactant powder to fluorocarbon provides a surfactant particulate dispersed throughout the fluorocarbon liquid.

During administration, the infant is placed in the right and left lateral decubitus positions while being mechanically or manually ventilated. Unlike other surfactant replacements in use that lack positive spreading coefficients and high density, fluorocarbon is unilaterally distributed in the lung. Since neonates are often difficult to intubate, only those individuals experienced in neonatal intubation should attempt this procedure. Mechanical ventilator usage and initial settings of breaths/minute, positive inspiratory pressures, positive-end expiratory pressure and inspiratory durations should be set initially as determined by the known standards for given infant weight and gestational ages, but should be monitored closely and altered accordingly as pulmonary function improves.

The use of partial liquid ventilation is not restricted to cases where lung surfactant supplementation is necessary. Any condition requiring facilitated oxygen delivery, for example, is amenable to use of partial liquid ventilation. Because the volume of fluorocarbon in the lung is such that liquid fluorocarbon is not exhaled by the patient into the ventilation equipment, conventional ventilation equipment can be used. This overcomes a major obstacle to liquid breathing as contemplated in the prior art.

In addition to oxygen delivery, fluorocarbons can be used to remove endogenous or foreign material from the interior of the lungs. Lavage can be practiced using fluorocarbons as a substitute for conventional saline solutions. In this procedure, oxygen is provided to the patient by the fluorocarbon liquid itself, permitting a more lengthy and less dangerous lavage procedure. Moreover, removal of lung surfactant through the lavage is not a major problem because of the lung surfactant properties of selected fluorocarbons. The lavage procedure is further facilitated by the density of the fluorocarbon. The density of these liquids is generally 2, that is, twice that of water; they therefore tend to displace the material to be removed. This material can then be removed by removing the fluorocarbon, or can be removed from the surface of the fluorocarbon on which it will generally float.

In addition to the lung surfactant properties, the density of the fluorocarbon can facilitate inflation of collapsed alveoli and other portions of the lung. Under the influence of gravity, the fluorocarbon will apply positive pressure above and beyond breathing pressure to inflate such collapsed portions of the lung.

Partial liquid ventilation according to the present invention is useful for a variety of medical applications. As a lavage, the technique is useful for meconium aspiration, gastric acid aspiration, asthma, cystic fibrosis, and pneumonia to remove adventitious agents. A fluorocarbon lavage may also be provided to patients with pulmonary alveolar proteinosis, bronchiectasis, atelectasis and immotile cilia syndrome. In addition, fluorocarbon may be used in emergency lavage procedures to remove food aspirates and other foreign materials.

Loss of lung resiliency can occur in both ARDS and RDS. The use of fluorocarbons in both of these syndromes is discussed above. In addition, lungs can become stiff from hydrocarbon aspiration, smoke inhalation, and lung contusions. Fluorocarbon therapy can be provided either as a surfactant supplement or for partial liquid ventilation to supply oxygen to a patient or to facilitate a therapeutic regime. Treatment of pulmonary fibrosis, emphysema, and chronic bronchitis can all benefit from fluorocarbon therapy.

It has been noted above that a fluorocarbon liquid may be supplied to a patient in combination with a powdered surfactant or as a route for pulmonary drug delivery. Antibiotics and antivirals may be provided in combination with a fluorocarbon liquid. For example, cytomegalovirus can induce life-threatening cases of pneumonia in immunocompromised patients. These individuals often require ventilation therapy. Fluorocarbon administration in combination with the guanosine nucleoside analog, 9-(1,3-dihydroxy-2-propoxymethyl)guanine, otherwise known as Ganciclovir or DHPG, may provide an effective therapy that could simultaneously inhibit vital replication and facilitate oxygen transport in the compromised lung.

In addition, anti-inflammatory agents could be added alone or in combination to the antimicrobial agents contemplated above. These anti-inflammatoryagents include, but are not limited to, steroid and steroid derivatives or analgesics. The fluorocarbon could be administered together with a bronchodilator including, but not limited to, Albuterol, isoetharines, perbuteral or an anti-allergenic agent.

The present invention permits full use of the partial liquid ventilation techniques described herein with conventional ventilation equipment. The apparatus is designed to minimize the equipment expense associated with partial liquid ventilation and to permit full gas ventilation or partial liquid ventilation as desired.

As illustrated in FIG. 1, the partial liquid ventilation device 10 of the present invention includes an endotracheal tube 12. The endotracheal tube 12 has a distal end 14 which is inserted into the trachea 16 of the patient. A perfluorocarbon (PFC) instiller 20 is also provided in association with the endotracheal tube 12 for introducing perfluorocarbon liquid 22 into the lungs 24 of the patient. Further, a PFC remover 26 is also provided in connection with the endotracheal tube 12 for removing perfluorocarbon liquid (and other fluid) from the lungs 24.

It is preferred that the PFC instiller 20 and the PFC remover 26 are of such size or location that they do not substantially inhibit the flow of breathing gas through the endotracheal tube 12, into and out of the patient's lungs 24. It is also contemplated that the instiller 20 and remover 26 can be combined into a single, dual lumen tube, or that with pulsed introduction and removal, that a single tube can function both as the instiller 20 and the remover 26.

One or more PFC reservoirs 30 are provided in the present invention. One PFC reservoir 30 is connected to the PFC instiller 20 for introducing perfluorocarbon liquid into the lungs 24 through the endotracheal tube 12. The same or different PFC reservoir 30 is connected to the PFC remover 26. Perfluorocarbon removed from the lungs 24 by the PFC remover 26 is collected in such a PFC reservoir 30 for disposal or for reuse.

In the illustrated schematic embodiment, a removal conduit 32 connects the PFC remover 26 with the PFC reservoir 30. Similarly, an instiller conduit 34 may connect the PFC reservoir 30 to the PFC instiller 20.

The present invention is adapted to permit introduction and removal of perfluorocarbon from the lungs 24 at the same time the patient is inhaling oxygen-carrying gas. In practice, perfluorocarbon may be continuously or periodically introduced into the lungs 24 through the instiller conduit 34 and the instiller 20. Preferably, the patient continues to breath throughout the process with the help of a gas ventilator 36 (which is in fluid connection with the proximal end 40 of the endotracheal tube 12). In one embodiment of the invention, a gas flow sensor 42 is provided in the path of gas moving from the ventilator 36 into the lungs 24 to monitor inhalation and expiration.

When the perfluorocarbon liquid 22 being introduced through the instiller 20 fills the lungs 24 (and, optionally, the endotracheal tube 12) to a level that brings the perfluorocarbon liquid in the lungs and trachea into contact with the PFC remover during exhalation or expiration, the PFC remover 26 removes perfluorocarbon from the patient while the PFC is in contact with the PFC remover.

In one preferred embodiment of the invention, a fast pump 44 is connected to the removal conduit 32 for moving perfluorocarbon liquid 22 which contacts the PFC remover 26 from the PFC remover 26 through the removal conduit 32 and into the PFC reservoir 30. The fast pump 44 can be operated continuously to remove perfluorocarbon liquid, lung debris, and (when liquid is not in contact with the PFC remover 26) gas out of the lungs and into the PFC reservoir 30. If a closed system is desired, and if the fast pump 44 is operated continuously, an air vent 46 may be provided to return air from the PFC reservoir 30 into the gas ventilator 36, the endotracheal tube 12, or the lungs 24. The fast pump 44 may alternatively pulsate. That is, it can operate on a timed basis (e.g., on for one minute, off for one minute) or, preferably, it can operate for the 10 to 30% of the breathing cycle that bridges the end of expiration and the beginning of inhalation. A controller 50 may be used to monitor the phase of the breathing cycle (e.g., through use of the gas flow sensor 42 or by direct connection to the gas ventilator 36). The controller 50 can, in turn, pulse the operation of the fast pump 44 (or other means for controlling the removal of perfluorocarbon through the PFC remover 26) to correspond to the breathing cycle.

A slow pump 52 may be connected to the instiller conduit 34 for moving perfluorocarb0n through the instiller conduit 34 through the instiller 20 into the lungs 24. The slow pump 52, if operated continuously, would introduce perfluorocarbon through the instiller 20 at a rate less than the fluid-moving capacity of the fast pump 44. Phrased differently, the fast pump 44 must be capable, during the time in which it is removing fluorocarbon through the removal conduit 32, of moving at least as much perfluorocarbon as the slow pump 52 introduces through the instiller conduit 34 (less any evaporation losses). It will be appreciated, therefore, that the fast pump 44 and the slow pump 52 combine to maintain a relatively constant volume of perfluorocarbon in the lungs. If an excess amount of perfluorocarbon enters the lungs, it will be removed by the fast pump 44 through the PFC remover 26. Alternatively, if the PFC level in the lungs is too low, little or no PFC will come in contact with the PFC remover 26 until the slow pump 52 in combination with the instiller 20 introduce sufficient perfluorocarbon into the lungs to bring the perfluorocarbon to the desired level.

Although the apparatus of the present invention will function well with continuous introduction of perfluorocarbon through the instiller 20, it may be desired to pulse the introduction of perfluorocarbon, either by cycling the slow pump 52 on and off at timed intervals, or actuating the slow pump 52 during a certain portion of the breathing cycle. In one preferred embodiment, the slow pump 52 operates only during inhalation. This has the advantage of permitting the gas flow into the lungs 24 to carry the perfluorocarbon liquid with it, and avoids undesired "blowing" of perfluorocarbon droplets into the gas ventilator during expiration.

The gas ventilator 36 can be a conventional gas ventilator of any suitable design. In one embodiment of the invention, however, a condenser 54 is connected to the gas ventilator 36. The condenser 54 employs suitable means (such as the illustrated refrigerated coil 56 for condensing perfluorocarbon gas to form liquid). A condenser reservoir 60 may be provided to capture the condensed liquid from the condenser 54. This condensed perfluorocarbon can then be reintroduced into the PFC reservoir 30 as indicated by the dashed line 62. Alternatively, this used perfluorocarbon can be held for recycling or disposal.

Although one particular configuration of the partial liquid ventilation device 10 is illustrated in FIG. 1, it will be appreciated that less complex or more complex versions of this device may be employed by following the present disclosure. A simpler version of the device, for example, can operate in conjunction with a conventional gas ventilator with no automated equipment for introducing and removing perfluorocarbon. In this simplest embodiment of the invention, the PFC reservoir to which the instiller 20 is connected may be elevated above the instiller 20 so that PFC can flow through the instiller 20 into the lungs 24 by gravity flow. The instiller 20 may comprise an appropriate metering device or flow restrictor to introduce perfluorocarbon into the lungs at a constant rate.

Similarly, the PFC reservoir 30 connected to the PFC remover 26 may be below the level of the PFC remover 26 so that all perfluorocarbon 22 coming into the contact with the PFC remover 26 can flow under the influence of gravity into the appropriate PFC reservoir 30. This gravity flow system is particularly appropriate in connection with the gas/liquid separator 64 illustrated in FIGS. 3 and 4.

With reference again to FIG. 1, means may be further provided for separating debris and aqueous material from the perfluorocarbon in the perfluorocarbon reservoir 30 which receives perfluorocarbon from the PFC remover 26. The apparatus and method of the present invention are effective in removing mucus and other debris from the lungs 24. Because the density of the perfluorocarbon liquid is generally approximately twice that of water, such debris and aqueous liquid will tend to float on the top of the perfluorocarbon, both in the lung 24 and the PFC reservoir 30. For this reason, it can easily be removed by the PFC remover 26 and it will be separated by flotation by the PFC in the PFC reservoir 30. Appropriate means can be provided for decanting, filtering, or otherwise removing the aqueous layer 66 from the fluorocarbon in the PFC reservoir 30. Such means can comprise means for decanting the aqueous layer (which contains lung debris as well as aqueous liquid), for filtering that material from the fluorocarbon, or by other appropriate means.

One embodiment of the invention separates aqueous material and debris from the perfluorocarbon in the PFC reservoir 30 by floatation. In this embodiment, it is preferred that the slow pump 52 remove perfluorocarbon liquid from the bottom 70 of PFC reservoir 30, or at least from a point below the aqueous layer 66.

If desired, the instiller conduit 34 may be connected to a filter 72 for removing any residual debris from the perfluorocarbon liquid being introduced into the lungs. The filter 72 is preferably a fluorocarbon-wetted or fluorocarbon-wettable filter, such as a teflon filter. Alternatively, a nonwoven water-wettable fiber filter could be used to separate debris from the fluorocarbon. Such filters of up to 20 µm pore size, more preferably up to 1.0 µm pore size, can remove both aqueous droplets and more substantial debris from the fluorocarbon liquid. Of course, the filter 72 may instead be connected to the removal conduit 32 to remove aqueous material and debris before collecting that material in the PFC reservoir 30.

The present invention also includes specialized partial liquid ventilation connectors for connection to the proximal end of a conventional endotracheal tube 12, as well as specialized endotracheal tubes especially adapted for use in partial liquid ventilation.

Means (not shown) may also be included in the fluorocarbon reservoir 30 for regulating the temperature of the fluorocarbon. Preferably, the fluorocarbon is maintained at physiological temperature; however, it is also contemplated that the fluorocarbon can be used to raise or lower the body temperature. It is particularly well adapted to this use, because of its location in the lungs. Thus, the method of the present invention includes increasing or decreasing the body temperature by adjusting the temperature of the fluorocarbon used in the partial liquid ventilation procedure.

FIG. 2 illustrates the use of a conventional endotracheal tube 12. The simple combination of endotracheal tube 12 and partial liquid ventilation coupler 74 is illustrated in FIG. 2. As illustrated, a conventional endotracheal tube 12 has a distal end 14 located inside the patient's trachea, a proximal end 40 located outside the patient, a proximal connector 76 at the proximal end 40 of the endotracheal tube 12, and an inflatable cuff 80, generally of annular construction, located near the distal end 14 of the endotracheal tube 12. The inflatable cuff 80, when inflated, anchors the endotracheal tube 12 in the desired location in the trachea 16 and provides a seal against the trachea so that all material entering or leaving the lungs must pass through the endotracheal tube 12.

In the embodiment illustrated in FIG. 2, the positive liquid ventilation (PLV) coupler 74 is adapted to connect directly to the proximal end connector 76 of the endotracheal tube 12. Thus, the distal end of the PLV coupler 74 connects to the proximal end of the endotracheal tube 12, and the proximal end of the PLV coupler 74 connects to the gas ventilator 36 (typically through tubing running from the gas ventilator to the patient). The connector 82 at the proximal end of the coupler 74 is advantageously the same as the proximal connector 76 on the endotracheal tube 12.

The coupler 74 preferably including a flow sensor 42 is described in connection with FIG. 1. Additionally, the coupler 74 has associated with it the PFC instiller 20 and the PFC remover 26. In the illustrated embodiment, the removal conduit 32 and the instiller conduit 34 are both incorporated into a double lumen tube 84 which extends through the PLV coupler 74 distally into the endotracheal tube 12. As previously mentioned, a single tube performing the functions of the instiller 20 and remover 26 is also contemplated. The particular location of the PFC instiller 20 and the PFC remover 26 at the distal end of the double lumen tube 84 is a matter of choice. For example, both the instiller 20 and the remover 26 could be located in the coupler 74 or at any point inside the endotracheal tube 12. In the illustrated embodiment, the double lumen tube 84 is adapted to extend distally into and through the endotracheal tube 12 to a point in close proximity to the distal end 14 of the endotracheal tube 12. It is preferred that the PFC instiller 20 is located at least one centimeter distally of the PFC remover 26. This reduces the amount of perfluorocarbon flowing out of the instiller 20 and immediately back into the remover 26. In FIG. 2, the instiller end 20 and the remover 26 are both located within about 5 to 10 cm of the distal end of the endotracheal tube 12. However, it will be appreciated that the instiller 20 and the PFC remover 26 can be located at the distal end 14 or further distal of the distal end 14 of the endotracheal tube 12. Alternatively, the instiller 20 can be located near the distal end 14 of the endotracheal tube and the remover 26 can be located a substantial distance proximally of the instiller 20. It is contemplated that the instiller 20 can be located near the distal end 14 of the endotracheal tube 12, and that the remover 26 can be located at any desired point proximally thereof, including location in the endotracheal tube 12 near the proximal end 40 thereof, or location in the coupler 74. Moreover, it is further contemplated that both the instiller 20 and the remover 26 can be located within the coupler 74.

Location of the remover 26 is dictated by the desired volume of perfluorocarbon employed in the partial liquid ventilation procedure of the present invention. If the remover 26 is located low in the trachea near the distal end 14 of the endotracheal tube 12, the amount of perfluorocarbon employed in the partial liquid ventilation procedure is approximately equal to the functional residual capacity of the lungs upon exhalation. By moving the PFC remover 26 proximally into the coupler 74, the amount of fluorocarbon 22 in the lungs 24 is increased by approximately the interior volume of the endotracheal tube 12.

It is further contemplated that an air vent 46 be provided in the coupler 74 of FIG. 2, and that the air vent 46 may be integral with the double lumen tube 84 (i.e., a triple lumen tube 84 can be used); alternatively, the air vent 46 may be separate.

Figure 4:
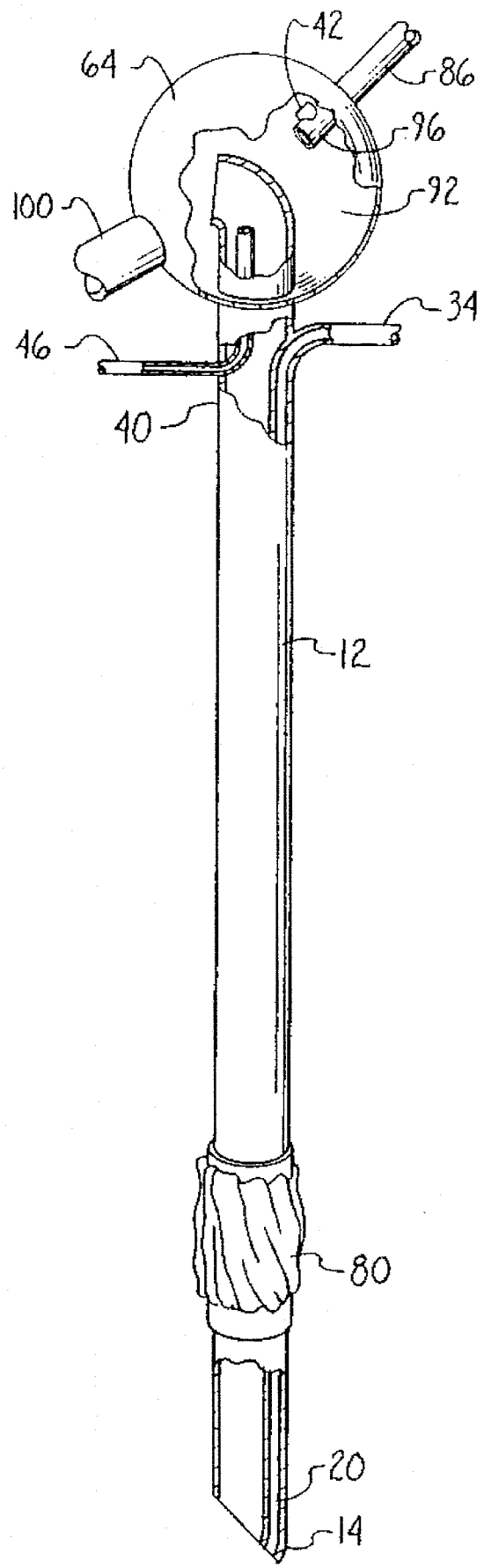
FIG. 4 is a perspective view of an integrated endotracheal tube/partial liquid ventilation connector with a gas/liquid separator at the proximal end.

Still another embodiment of the invention provides a gas/liquid separator 64 at the proximal end 40 of the endotracheal tube 12. The gas/liquid separator 64 may be incorporated into the PLV coupler 74, as illustrated in FIG. 3, or may be integrated into the endotracheal tube 12, as illustrated in FIG. 4.

With reference to FIG. 3, the gas/liquid separator 64 comprises a chamber of substantially greater width than the gas ventilation tubing 86 running to the gas ventilator 36 and the endotracheal tube 12. In the embodiment of the gas/liquid separator 64 illustrated in FIG. 3, the PLV coupler 74 comprises a cylindrical portion 90 (which can be of cylindrical cross-section or other desired cross-section). The cylindrical portion 90 is adapted to connect to the proximal end of the endotracheal tube 12. An instiller conduit 34 is provided in the cylindrical portion 90, and the cylindrical portion 90 also supports and locates the instiller 20 at the desired location (as discussed above). The proximal end of the cylindrical portion 90 terminated inside the separator chamber 92. The separator chamber 92 is preferably spherical, although partially spherical, rectangular, or other configurations may be used if desired. All fluid exiting the proximal end of the cylindrical portion 90 as it leaves the lungs enters the gas/liquid separator. This fluid is gravitationally separated in the separator chamber 92. The PFC remover 26 is in fluid communication with the interior of the separator chamber 92 and is adapted to drain the liquid from the separator chamber 92. Although the PFC remover 26 may be in a fixed location (as discussed hereafter in connection with FIG. 4), the embodiment illustrated in FIG. 3 has a movable PFC remover 26. In that illustrated embodiment, the PFC remover 26 is located inside the separator chamber 92 at the end of a flexible drain conduit 94. The PFC remover is weighted so that it locates itself at or near the lowest point of the separator chamber 92. This particular embodiment is useful in situations where the patient may move during the partial liquid ventilation procedure, and ensures that the drain is always located at or near the bottom of that chamber so that liquid can be effectively removed from the separator chamber 92. In the embodiment of FIG. 3, the proximal end of the cylindrical portion 90 is located near the center of the separator chamber 92. This ensures that the proximal end of the cylindrical portion 90 is located above the liquid level regardless of the patient's position.

A gas conduit 96 is also connected to the interior of the separator chamber 92 for introducing and removing gas into and out of the separator chamber 92, as that gas is driven by the gas ventilator 36. The gas conduit 96 is connected through the gas vent tubing 86 to the gas ventilator 36. The distal (closest to the patient) end of the gas conduit 96 is preferably also located near the center of the gas/liquid separator of FIG. 3. This again ensures that the gas conduit 96 is not submerged in perfluorocarbon liquid during performance of partial liquid ventilation.

The air vent 46 may advantageously be connected either to the cylindrical portion 90 or the separator chamber 92. Preferably, the air vent terminates at a point near the center of the separator chamber.

Another embodiment of the gas/liquid separator is illustrated in FIG. 4. This gas/liquid separator is similar to the one described in connection with FIG. 3. However, it is adapted to be used when the patient can undergo a limited range of movement during the procedure. As illustrated in FIG. 4, the PFC remover 26 comprises a relatively large-diameter drain 100 for draining liquid out of the bottom of the separator chamber 92. The proximal end of the cylindrical portion 90 and the distal end of the gas conduit 96 may be located at any point desired inside the chamber 92, so long as they are located above the anticipated liquid level in the separator chamber 92. Preferably, the proximal end of the cylindrical portion 90 and the gas conduit 96 are both located in the upper portion of the separator chamber 92. It is preferred that the proximal end of the cylindrical portion 90 be directed away from the opening of the gas conduit 96 to prevent inadvertent travel of perfluorocarbon liquid from one opening to another. In the embodiment illustrated in FIG. 4, the cylindrical portion 90 actually comprises the proximal end 40 of the endotracheal tube 12. Moreover, as shown in FIG. 4, the air vent and the instiller are directly connected to the interior of the endotracheal tube 12. If desired, the air vent 46 and the instiller 20 can be formed integrally (as through molding or extrusion) with the endotracheal tube 12.

Although particular embodiments of the partial liquid ventilation device 10, the gas/liquid separator 64, the positive liquid ventilation coupler 74, and the endotracheal tube 12 have been described, it will be appreciated by those of ordinary skill in the art that numerous variations are possible within the spirit of the present invention. For example, other forms of gas/liquid separators are known in the art and may be used in place of the illustrated versions. As previously explained, the actual location within the system of the PFC remover 26 and the PFC instiller 20 can be varied.

It will further be appreciated that the method of using the apparatus of the present invention eliminates the need to alternate between full liquid ventilation (which requires extensive and complicated apparatus) and partial liquid ventilation. The method of the present invention has the particular advantage of permitting introduction of perfluorocarbon into the lung and removal of perfluorocarbon out of the lung while a breathing gas is simultaneously moving into and out of the lungs.

It will further be appreciated that the method of the present invention includes a lung lavage. By introducing and removing perfluorocarbon according to the present invention while the patient is breathing, the tidal forces of breathing and the turbulent mixture of breathing gas and perfluorocarbon in the lung itself will dislodge and ultimately remove undesired materials from the interior of the lung. Lavage will be particularly effective if the volume of perfluorocarbon circulated into and out of the lung is substantial. While relatively small quantities of perfluorocarbon exchange can be effective (e.g., 0.5 to 5 ml per breathing cycle), it is contemplated that even larger quantities of perfluorocarbon can be introduced and removed as desired for particular results. The adult human lung has a functional residual capacity of approximately 2.5 liters. The fully inflated adult human lung has a capacity of about 3 liters. Thus, the tidal volume of air moving in and out of the lung during each breathing cycle is approximately 500 ml. It is contemplated that quantities of perfluorocarbon up to 50% of the tidal volume, in other words, up to 250 ml for breathing cycle (for an adult human) can be introduced and removed from the lungs in accordance with the present invention. It is preferred, however, that much smaller volumes are exchanged. A particularly preferred amount for lavage in the adult human is 5% to 10% of the tidal volume, or from 25 to 50 ml per breathing cycle. The absolute numbers will vary, of course, for infants, children, and nonhuman animals.

The scope of the present invention should be determined by reference to the following claims, without restriction of those claims to the embodiments specifically described or illustrated in the specification and drawings.

What is claimed is:

1. An apparatus for partial liquid ventilation of a patient, comprising:

a source of a biocompatible liquid suitable for ventilation of a patient;

a first relatively small conduit adapted for connection to an airway of a patient, said first conduit operatively connected to said liquid source in such a manner as to introduce a first volume of said liquid into a portion of a lung already containing a second volume of said liquid;

a source of breathing gas; and a relatively large conduit adapted for connection to an airway of a patient, said large conduit operatively connected to said gas source in such a manner as to deliver a breathing gas to said portion of said lung containing said liquid simultaneous with but separate and apart from said liquid introduction in the same portion of a lung, whereby said breathing gas mixes with and oxygenates a second volume of liquid in a lung.

2. The apparatus of claim 1, further comprising a second relatively small conduit adapted to remove a volume of said liquid from a lung while a patient is simultaneously breathing a gas.

3. The apparatus of claim 2, wherein the second conduit is adapted to remove excess liquid to maintain a relatively constant volume of liquid in a lung while a patient is simultaneously breathing gas.

4. The apparatus of claim 2, wherein the second conduit is adapted to remove said liquid during a portion of the breathing cycle in which a lung is substantially deflated.

5. The apparatus of claim 2, wherein said second conduit includes an inlet adapted to be positioned in a patient's trachea or in close proximity thereto to remove liquid from a trachea that comes in contact with said inlet.

6. The apparatus of claim 5, wherein the first small conduit is adapted to continuously introduce liquid, and wherein the second conduit is adapted to remove liquid at a rate greater than or equal to the rate of introduction.

7. The apparatus of claim 5, wherein said relatively large conduit comprises an endotracheal tube in which said inlet is located, said tube adapted to be located at a fixed position in the trachea, said inlet adapted to remove liquid while such liquid is in contact with said inlet so that during the breathing cycle at the end of expiration, the liquid level in the pulmonary system of the patient is approximately at the level of said inlet.

8. The apparatus of claim 7, wherein the first and second conduits are attached to said endotracheal tube.

9. The apparatus of claim 7, further comprising a gas ventilation device connected to said endotracheal tube and adapted to introduce breathing gas to the lungs and to remove gas from the lungs.

10. The apparatus of claim 9, further comprising a fluorocarbon reservoir for receiving fluid removed from the patient by said removing means and a gas vent connecting the reservoir to the endotracheal tube to permit outside equalization of pressure between the endotracheal tube and the fluorocarbon reservoir.

11. The apparatus of claim 9, further comprising a gas flow sensor associated with said endotracheal tube and a means responsive to the sensor that pauses the introduction of liquid into the lung during exhalation.

12. The apparatus of claim 9, wherein said second conduit includes a gas flow sensor associated with said endotracheal tube that pauses the removal of liquid from the lung during inhalation.

13. The apparatus of claim 2, further comprising a reservoir into which said second conduit directs the removed liquid.

14. The apparatus of claim 13, wherein the first conduit is connected to the reservoir in such as way as to remove liquid from said reservoir for introduction into the lungs.

15. The apparatus of claim 14, further comprising a separator for separating contaminating material from the liquid in the reservoir prior to reintroduction into the lungs.

16. The apparatus of claim 15, wherein said liquid is at least one fluorocarbon liquid and said separator is adapted to separate floating contaminants from a fluorocarbon liquid.

17. The apparatus of claim 15, wherein the reservoir has a fluorocarbon/aqueous aspirant interface and wherein the first conduit removes fluorocarbon liquid from the reservoir from a point below the level of the fluorocarbon/floating contaminant interface.

18. The apparatus of claim 2, further comprising a gas pathway for gas exiting a patient's lungs through the large conduit, and a gas/liquid separator interposed in said gas pathway.

19. The apparatus of claim 18, wherein said gas/liquid separator is adapted to separate fluorocarbon liquid exiting the lungs exhaled by the patient, so that at the end of exhalation the liquid level in the patient's breathing passageway extends substantially up to but not beyond the gas/liquid separator.

20. The apparatus of claim 18, wherein said apparatus further includes an endotracheal tube connected to said gas/liquid separator.

21. The apparatus of claim 1, wherein said first conduit is adapted to continuously introduce said liquid.

22. The apparatus of claim 1, wherein said first conduit is adapted to introduce said liquid simultaneously with the inhalation of said gas.

23. The apparatus of claim 1, further comprising a flow controller adapted to pulse the introduction of liquid into the lungs in synchrony with a portion of the breathing cycle.

24. The apparatus of claim 2, further comprising a flow controller adapted to pulse the removal of liquid from the lungs in synchrony with a portion of the breathing cycle.

25. The apparatus of claim 1, wherein said apparatus includes a temperature control device to control the temperature of the liquid introduced into the lungs.

26. A method for partial liquid ventilation, comprising:
    introducing a first volume of liquid into a portion of a lung already containing a second volume of such liquid; and
    simultaneously delivering an oxygen containing breathing gas, separate and apart from said first volume of liquid, into said portion of patient's lung containing said second volume of liquid, whereby said breathing gas mixes with and thereby oxygenares said second volume of liquid in a patient's lung.

27. The method of claim 26, further comprising a removing step of positioning a liquid remover having an inlet in a trachea of a patient or in close proximity thereto, and removing liquid from an airway of patient that rises to the level of said inlet during the portion of the breathing cycle when patient's lungs are substantially deflated.

28. The method of claim 27, further comprising inserting an endotracheal tube having a distal end and a proximal end wherein said distal end of said endotracheal tube is located in a patient's trachea and positioning the inlet of the liquid remover between a distal end of the trachea and about the proximal end of the endotracheal tube.

29. The method of claim 28, comprising maintaining the sum of said first and second volumes of liquid in the pulmonary system of the patient at about the functional residual capacity of the patient's pulmonary system plus the internal volume of the trachea and endotracheal tube.

30. The method of claim 27, further comprising removing liquid from the patient in at least a portion of said removing step at a rate equal to or greater than the average rate of introduction of liquid into the lungs.

31. The method of claim 27, further comprising the step of condensing evaporated liquid from breathing gas exhaled by the patient.

32. The method of claim 27, further comprising the step of collecting the liquid removed from the patient.

33. The method of claim 32, further comprising the steps of separating contaminants from the collected liquid, and reintroducing that liquid into the lungs of the patient.

34. The method of claim 33, comprising providing a fluorocarbon as said liquid and the separating step is accomplished by the step of floating said contaminants on said fluorocarbon.

35. The method of claim 32, wherein said collecting step comprises filtering the liquid collected from a patient to separate debris or aqueous materials from the collected liquid.

36. The method of claim 26, providing an oxygen-carrying fluorocarbon as said first and second volumes of liquid.

37. The method of claim 26, comprising maintaining the sum of said first and second volumes of liquid in the pulmonary system of the patient at about the functional residual capacity of the patient's pulmonary system.

38. The method of claim 26, additionally comprising the step of introducing a pharmacologic agent into the lung while performing the method.

39. In a liquid breathing system having a means for introducing liquid perfluorocarbon into a lung and a means for oxygenating the liquid perfluorocarbon with an oxygen-containing gas, the improvement comprising:
    means for collecting said oxygen-containing gas from lung after it has been used for oxygenating said liquid perfluorocarbon, said used oxygen-containing gas further comprising evaporated liquid perfluorocarbon; and
    a perfluorocarbon condenser in said system adapted to remove said evaporated liquid perfluorocarbon from said collected oxygen-containing gas.

40. The apparatus of claim 39, further comprising a means for reintroducing condensed perfluorocarbon into the lung.

41. A liquid breathing method, comprising:
    introducing liquid perfluorocarbon into a patients lung;
    oxygenating said liquid perfluorocarbon with an oxygen-containing gas, to provide a used oxygen-containing gas comprising evaporated liquid perfluorocarbon;
    collecting said used oxygen-containing gas comprising evaporated liquid perfluorocarbon from said lung; and
    condensing said evaporated liquid perfluorocarbon from said collected used oxygen-containing gas.

42. The method of claim 41, further comprising the step of reintroducing said condensed fluorocarbon into the lung.

43. The method of claim 41, wherein said oxygen-containing gas is collected after passing through said lung.

44. The method of claim 41, wherein said oxygen-containing gas is vented to the atmosphere.

45. An apparatus for performing partial liquid breathing, comprising:

an endotracheal tube adapted for attachment to a gas ventilator;

a perfluorocarbon delivery conduit feeding into said endotracheal tube in such a manner that discrete breathing gas and liquid perfluorocarbon phases can simultaneously move into the same portion of a patient's lungs through said endotracheal tube; and a source of liquid perfluorocarbon connected to said delivery conduit through a flow controller that is responsive to gas flow from said ventilator.

46. The apparatus of claim 45, wherein said flow controller is adapted to pulse the introduction of liquid into the lung in synchrony with a portion of the gas breathing cycle.

47. In a method for partial liquid breathing in which breathing gas and liquid perfluorocarbon are simultaneously present in the same portion of a patient's lung in discrete phases, and said breathing gas first physically mixes with and oxygenares said liquid perfluorocarbon in the lung as said breathing gas moves into and out of the lung in a gas breathing cycle, the improvement comprising:

pulsing the introduction or removal of liquid perfluorocarbon from the patient's lungs in synchrony with said gas breathing cycle.

48. The method of claim 47, wherein additional liquid perfluorocarbon is introduced in synchrony with inhalation.

49. The method of claim 47, wherein liquid perfluorocarbon is removed from the lungs in synchrony with exhalation.

* * * * *